US005238844A

United States Patent [19]

Wight et al.

[11] Patent Number: 5,238,844

[45] Date of Patent: Aug. 24, 1993

[54] SLUDGE DIGESTER

[75] Inventors: Jeffrey L. Wight, Salt Lake City; Lynn W. Cook, Fruit Heights, both of Utah

[73] Assignee: Baker Hughes Incorporated, Houston, Tex.

[21] Appl. No.: 666,800

[22] Filed: Mar. 8, 1991

Related U.S. Application Data

[63] Continuation-in-part of Ser. No. 492,776, Mar. 12, 1990, Pat. No. 5,092,482.

[51] Int. Cl.[5] ..................... C12M 1/00; C12M 1/36

[52] U.S. Cl. ..................... 435/287; 435/289; 422/184; 210/603; 210/DIG. 9; 220/217

[58] Field of Search ..................... 435/3, 287, 289, 299, 435/313-316, 801, 813, 167; 422/106, 184; 48/197 A; 210/603, 218, DIG. 9, 188; 220/216, 217, 220, 221, 222, 224, 225, 226, 227; 147/198; 71/8, 10

[56] References Cited

U.S. PATENT DOCUMENTS

| | | | |
|---|---|---|---|
| 1,714,209 | 5/1929 | Bohnhardt | 220/217 |
| 1,735,461 | 11/1929 | Haupt | 220/224 |
| 1,906,685 | 5/1933 | Wiggins | 220/217 |
| 1,919,634 | 7/1933 | Haupt et al. | 220/227 |
| 1,930,953 | 10/1933 | Hampton | 220/224 |
| 1,989,589 | 1/1935 | Fischer et al. | 210/DIG. 9 |
| 2,061,175 | 11/1936 | Staber | 220/225 |
| 2,132,837 | 10/1938 | Talbot | 210/DIG. 9 |
| 2,541,090 | 2/1951 | Orr et al. | 220/217 |
| 2,679,477 | 5/1954 | Kivari et al. | 210/608 |
| 3,123,445 | 3/1964 | Heath | 422/106 |
| 3,181,731 | 5/1965 | Ellis | 422/106 |
| 3,288,295 | 11/1966 | Kelly | 210/DIG. 9 |
| 4,166,835 | 9/1979 | Anderson | 210/DIG. 9 |
| 4,173,291 | 11/1979 | Hills | 220/225 |
| 4,391,705 | 7/1983 | Cook et al. | 210/DIG. 9 |
| 4,648,968 | 3/1987 | Gutler | 210/DIG. 9 |
| 4,710,292 | 12/1987 | Devos | 210/DIG. 9 |
| 5,092,482 | 3/1992 | Wight et al. | 210/DIG. 9 |

*Primary Examiner*—Michael G. Wityshyn
*Assistant Examiner*—William H. Beisner
*Attorney, Agent, or Firm*—Trask, Britt & Rossa

[57] ABSTRACT

A sludge digester having a main tank in conjunction with a gas-holding cover is disclosed. The cover includes a roof and a depending sideskirt which telescopes in relationship to the main tank. Positioned at the bottom edge of the sideskirt are a multitude of ballast members. A chamber, adapted to contain a quantity of liquid, is associated with the main tank. The sideskirt and the ballast members are submerged within the liquid contained within the chamber to form a gas tight seal of the cover with the main tank. The chamber also includes a system for maintaining a predetermined liquid level in the chamber dependent on the position of the ballast members in the chamber.

4 Claims, 9 Drawing Sheets

SLUDGE DIGESTER

This application is a continuation-in-part of copending application Ser. No. 492,776 filed Mar. 12, 1990, now U.S. Pat. No. 5,092,482 having the same inventors and assignee, entitled "SLUDGE DIGESTERS WITH SEPARATE LIQUID CHAMBERS TO BUOY BALLAST MEMBERS."

BACKGROUND OF THE INVENTION

1. Field

The invention relates to sludge digesters of the gas-holding type having a telescoping cover which floats on an envelope of gas generated by decomposing sludge. The cover typically has a top (roof) and a cylindrical sidewall. Such digester covers further have ballast members which are generally formed of concrete. These depend into the sludge which has some buoyant effect upon the ballast members to create a differential gas pressure in the digester between the submerged and emerged conditions of said ballast members.

2. Technology Background

Ballasted, gas-holding, sludge digesters for digesting municipal waste are well-known in the art. U.S. Pat. No. 4,391,705 to Cook, et al. discloses a uniquely ballasted sludge digester of a gas-holding type. The ballast members of Cook, et al. contain cavities so that sludge fills the cavity to increase the ballast weight as the ballast members emerge from the sludge surface. The Cook, et al. sludge digester has been identified by its manufacturer as a "Hydroballast" TM Digester.

Prior to the development of the sludge digesters of the type disclosed in the Cook, et al. patent, it was common to use gas-holding covers having solid concrete blocks attached to the lower end of the sideskirt on the interior surface to add extra weight to the cover to increase the pressure of gas contained within the digester. When the concrete block ballasts were submerged in the sludge, a buoyant force was exerted by the sludge upon the ballast members according to Archimedes principal. Concrete used in ballast members generally has a density of about 150 pounds per cubic foot. A cubic foot of concrete in a submerged condition in sludge having a specific gravity of about 1.0 has an effective weight which is reduced by the weight of a cubic foot of sludge (about 62.4 pounds per cubic foot). Thus, in a submerged condition, one cubic foot of a solid concrete ballast exerts a downward force of about 87.6 pounds.

When the ballast members of a gas-holding digester cover emerge from the sludge, then the effective weight of the concrete is its normal density, i.e., about 150 lbs/ft$^3$. Thus, the total weight of the cover is significantly greater when the ballast members are in an emerged condition than when the ballast members are in a submerged condition. This creates a gas pressure differential between the submerged and emerged positions of the ballast. Typically, the operating pressure of the digester is that of the ballast when it is raised from the corbels but still in a submerged condition. When the ballast members are fully emerged from the sludge, the pressure generated is usually at or above the relief valve settings so that typically the ballast members are never fully emerged from the sludge without the relief valves on the cover relieving the pressure of the gas.

Gas storage tanks which employ telescoping covers are known in the petroleum industry wherein volatile liquids such as gasoline are frequently stored in tanks which have a floating cover. In this instance, the cover floats on an envelope of vapors generated by evaporation of gasoline and other volatile liquids. To eliminate evaporation losses which may occur in the annular "gap" which exists between the cover and the tank in which the cover telescopes, various types of roof seals have been developed. Exemplary of these roof seals are the seals disclosed in patents to Haupt, et al., U.S. Pat. No. 1,919,636; Hills, U.S. Pat. No. 4,173,291; and Staber, U.S. Pat. No. 2,061,175.

The type of roofs disclosed in Haupt, et al. and Hills are ones in which the roof floats directly upon the liquid. The cover disclosed in Staber, however, floats upon an envelope of vapor caused by evaporation of the volatile liquids contained in the tank. The device of Staber is described as a gasometer roof tank and uses a circumferential well located on the exterior of the main tank to hold water to effect a seal between the gases which are typically at a pressure of three inches water column (col. 4, line 22) on the interior and the atmosphere. The device of Staber also provides for the collection of volatile condensate in the well.

Seal troughs have been used because of the volatility of liquids within a tank, e.g., gasoline. The sole purpose of a seal trough, either with a fixed or floating cover, is to provide a system for preventing a vapor or gas from escaping from under the cover to the atmosphere. The depth of such a trough with a floating cover is equivalent to the length of travel of the cover plus a liquid column height equal to the cover pressure which, as indicated in Staber, is often in the range of a few inches water column. The width of a seal trough need only be minimal to accommodate a thin steel sideskirt.

Another type of tank used in the petroleum industry is disclosed in Bohnhardt, U.S. Pat. No. 1,714,209, wherein a sealing trough is located on an external wall of the tank to accommodate a short sideskirt of the cover to permit the cover to telescope over a small vertical distance without losing the effect of the liquid seal. As illustrated in FIGS. 1 and 2 of Bohnhardt, the trough is very small in comparison to the tank dimensions. The trough, roof, and sideskirt are structured so the sideskirt is positioned in the center of the trough.

The Bohnhardt tank is designed to hold petroleum vapors at a substantially constant pressure. Bohnhardt indicates that ballast could be added to the roof. The roof is prevented from rotating by columns located within the tank, and the roof is supported in an at-rest condition by other posts located within the tank.

In sludge digesters, water seals have been used with some fixed covers. Generally, sludge digester gas holder covers which float on an envelope of gas have a sideskirt and ballast immersed in the sludge liquid which further acts as a seal. Various types of seals have been used with sludge digester floating covers such as those disclosed in U.S. Pat. No. 1,735,461 (Haupt), U.S. Pat. No. 1,930,953 (Hampton), U.S. Pat. No. 1,919,634 (Haupt, et al.), and U.S. Pat. No. 4,173,291 (Hills).

Gas-holder telescoping covers of the type disclosed in Kelley, U.S. Pat. No. 3,288,295 and Fisher, et al., U.S. Pat. No. 1,989,589, were generally heavier than the more structurally sophisticated covers which have recently been designed and utilized. Concurrently, with the design of lighter covers has been the requirement for increased operating gas pressure. Gas pressures of from six inches of water and frequently from eight inches or more, up to fifteen inches, are relatively common with modern sludge digesters.

While the covers of Fisher utilized concrete ballast, the amount of concrete ballast used in a modern gas-holding cover is much greater. The need for greater ballasting led to the development of the unique ballast disclosed in Cook, et al. Increased ballast weight has resulted in the use of very large concrete ballast members. The use of such large ballast members, including those of the Cook, et al. type within a large sludge tank, has generally been readily feasible although concerns over grit accumulation in the Cook, et al. type ballast have existed and increased structural support for such large ballasts has been required. Corrosion of ballast support members within the digester can be a problem. Corrosive failure of ballast support members can and has resulted in some instances of digester operation in the ballast members being dumped in the sludge, causing the cover to tilt and bind.

Gas-holding sludge digesters have been ballasted in the manner illustrated in Fisher, et al. In practice, the sideskirts of such covers are usually constructed quite long so to maintain the ballast in a submerged condition in the fluctuating level of sludge within the digester. The cover of Fisher, et al. was ballasted with a concrete ballast member in the form of a continuous ring having a sloped top. The sloped top on the ballast ring was to prevent accumulation of grit and silt on the top surface of the ballast. The ballast member and its supports are generally submerged or partially submerged in the sludge. The sludge contains organic and inorganic liquids and solids and is corrosive and toxic. The immersion of the sideskirt in the sludge exposes the sideskirt, ballast supports, roller guides, and the like to gritty, corrosive conditions.

Water troughs external to a fixed cover have been used as seals. Such troughs are situated adjacent the upper edge of the main tank digester usually on the outside of the main tank wall. The cover is fixed to the upper edge of the main tank wall and has a very short skirt which extends downward into the trough. The purpose of the skirt is to cause the gas envelope to be in contact with the water seal. The trough is filled with water to create a water seal to prevent gas on the inside of the cover from escaping to the atmosphere. Such troughs are usually no deeper than about three feet and are about one foot in width.

A sludge digester employing a liquid seal trough structured to accept a vertically moveable sideskirt is disclosed in U.S. Pat. No. 4,166,835 to Anderson. The trough of Anderson being structured to permit also rotary motion of the sideskirt. As illustrated in the figures of Anderson, a very narrow trough was employed.

The tank of Anderson employs a central guide post and a roof member having a large central pipe or tube which fits over the post to maintain the roof in a central location with respect to the tank. The roof of Anderson projects beyond the sealing trough with a second sideskirt depending from the edge of the roof. The roof of Anderson is supported by the tank wall and the wall of the trough. The structure of the roof of Anderson is very similar to fixed roof digesters which use a liquid seal well and have the roof rest on the tank and well walls. The well or trough of Anderson is quite narrow and is only sufficiently wide enough to accommodate the sideskirt thereby having a minimum amount of water in the trough.

Launders, which are liquid overflow troughs, are illustrated in U.S. Pat. No. 2,679,477 to Kivari, et al. Such troughs are located at the upper lip of the tank on the outside surface of the tank wall. These are relatively small in comparison to the tank.

Neither launders, fixed roof seal troughs, nor seal troughs for telescoping covers are sufficiently large or adapted to accommodate the large dimensioned ballast members used in the higher pressure gas-holding sludge digesters presently being constructed.

SUMMARY OF THE INVENTION

The instant invention comprises a sludge digester having a main tank in conjunction with a gas-holding cover having a roof and depending sideskirt which telescopes in relationship to the main tank. At the bottom edge of the sideskirt, which typically has a cylindrical shape, are located a multitude of ballast members usually constructed of concrete having a density significantly greater than water. The main tank has a separate annular chamber, either internal or external to the main sidewall of the tank, to hold the liquid in which the sideskirt and ballast members are submerged. The sideskirts are equipped with rollers or other guide means which function to stabilize the cover during its telescoping travel within the tank.

Sludge digesters generally operate in a dynamic condition. Typically, fresh sludge is continuously entering the digester while sludge which is decomposed exits the digester either continuously or periodically. Gas is continually evolving within the digester due to the decomposition of organic matter within the sludge. The rate at which gas evolves is generally dependent upon the amount and type of organic matter in the sludge, the temperature of the sludge, the concentration and type of bacteria in the sludge as well as other minor factors such as pH, heavy metal hydroxide concentration, and sludge conditions. The inflow and outflow rate of sludge and decomposition rate of the sludge may not always be the same. Thus, the level of sludge within the digester may rise and fall. Assuming a constant gas pressure within the tank, rising and falling of the sludge level will affect the position of the cover causing it to rise and fall with the sludge level. The cover also rises and falls as the pressure or volume of gas changes, for example, as gas is withdrawn or as gas generation rate changes.

DETAILED DESCRIPTION OF THE INVENTION

The instant invention relates to sludge digesters which have a floating cover which floats on an envelope of gas. These sludge digesters are generally referred to as gas-holding sludge digesters. Such sludge digesters are composed of a main tank, generally of a cylindrical form and generally formed of concrete, and a steel cover formed of a dish-shaped top (roof) and cylindrical sidewall which telescopes in relation to the main digester tank. The cover is generally ballasted with ballast members suspended from the cylindrical sidewall (sideskirt) near its lower edge.

Further description of the invention may be facilitated by reference to the attached drawings.

Figure 1:
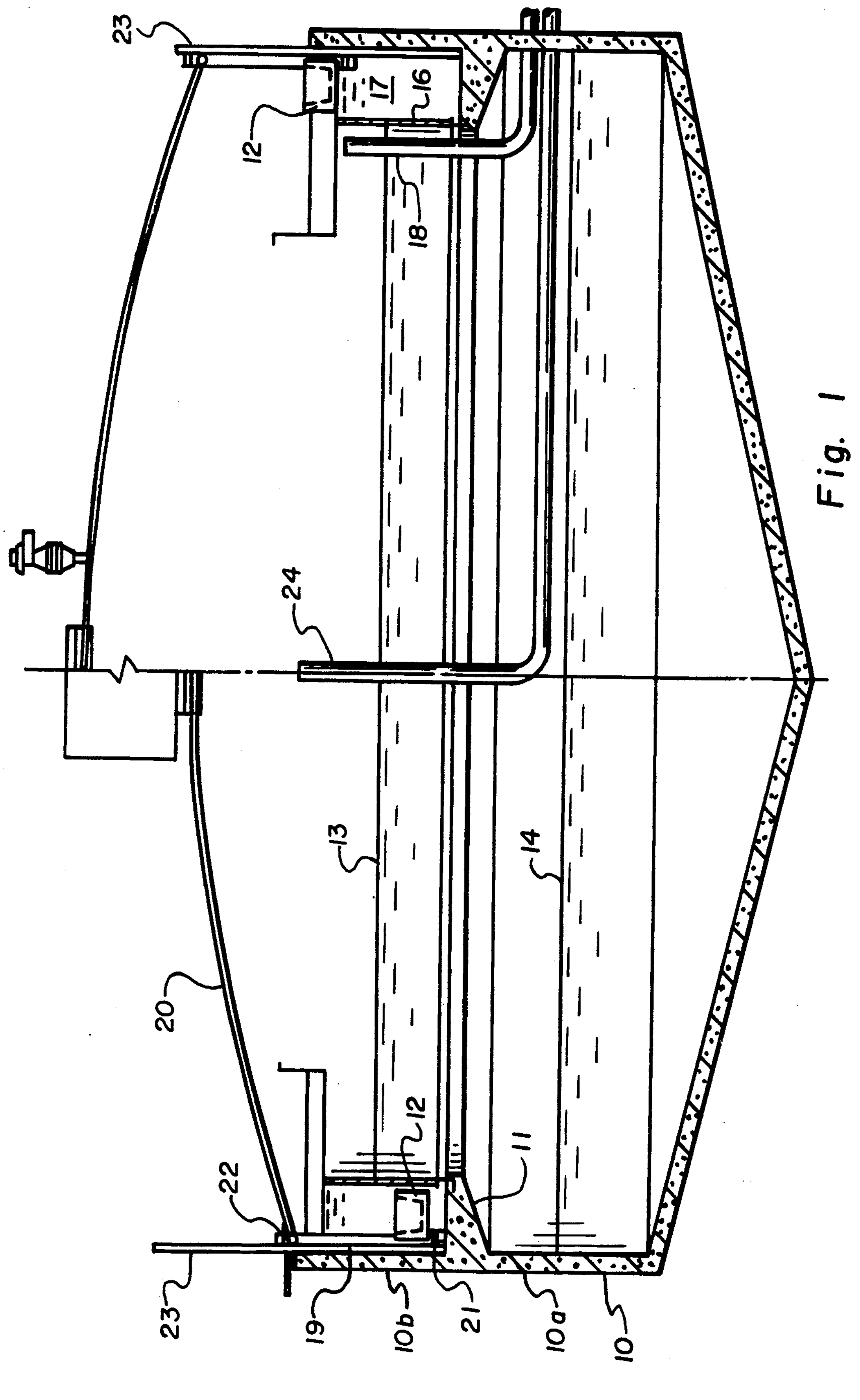
FIG. 1 is a sectional, elevational view of a digester of the instant invention.

A sectional, elevational view of the digester of the instant invention is illustrated in FIG. 1. The digester has a tank wall 10 which is generally a large, cylindrical, concrete structure frequently from 20 although typically from 50 to 125 feet or more in diameter. A corbel 11 is an integral part of the tank wall 10. In the instant invention, the corbel is an extended corbel wider than the ballast member 12 and is an annular ring, circumscribing the entire interior of the main tank wall 10. The tank wall 10 of the instant invention generally comprises two portions, a lower portion 10*a*, which is below the corbel 11, and an upper portion 10*b*, which is above the level of the corbel. The portion of the tank wall 10*a*, below the corbel, generally is filled with sludge although, as indicated by lines 13 and 14, the level of sludge in the tank may vary considerably during operation with the sludge level normally being at a height well above the corbels. An overflow pipe 15 is installed such that the top of the overflow is slightly lower than the interior sidewall 16 of the liquid ballast bath 17 so that sludge does not overflow into the liquid ballast bath 17.

The wall member 16 in FIG. i is a steel cylindrical wall which is embedded within the free end of corbel 11 and completely circumscribes the interior of the digester and is concentric with the tank wall 10 and spaced from tank wall portion 10*b* to form a ballast bath (buoyant liquid chamber) 17. The spacing between interior wall 16 and tank wall portion 10*b* is greater than the width of the ballast member, for example, guide members, and any structure associated with the ballast member as well as the thickness of the sideskirt. The sideskirt 19 is a cylindrical steel member depending from the domed cover 20.

The cover illustrated in FIG. 1 has rollers 21 and 22 which interact with the extended upright roller guide 23 to guide the cover as it telescopes upwardly and downwardly in the main tank. Relief valve settings are set so that typically the ballast members are never fully emerged from the sludge without the relief valves relieving the pressure of the gas. If relief valves are not used or do not function, the cover will keep rising as pressure increases until gas escapes under the edge of the sideskirt. While this is generally undesirable, the rising of the cover is self-limiting.

Sludge liquid within the digester has heretofore conventionally been the liquid in which the ballast members are submerged. The sludge liquid generally has a specific gravity which is within a few percent of the same specific gravity as water.

In the instant invention, as illustrated in FIG. 1, the ballast members are submerged in water or other liquid which is separated from the sludge by an interior wall 16. The ballast members rise and fall in the ballast bath. The ballast bath will generally be water although other liquids could be utilized. The sideskirt and rollers of this invention are also removed from contact with sludge, which has many advantages. Sludge is corrosive, toxic and gritty. Such an environment is inhospitable to metal, especially moving metal components. Sludge also stains and corrodes the sideskirt.

The ballast members illustrated in FIG. 1 have a cavity in which to contain liquid from the ballast bath. Other types of concrete ballast members such as a solid concrete block either of normal density concrete having the density of about 150 pounds per cubic foot or lightweight concrete having a density substantially less than 150 pounds per cubic foot may be used in the invention. The ballast members are attached to and supported by the sideskirt. Cantilevered arms attached to or near the lower edge of the sideskirt project away from the sideskirt to provide ballast supports. In conventional sludge digesters, such ballast supports have always extended interiorly of the sideskirt and have been immersed in the corrosive sludge environment.

The gas is extracted from the tank by gas withdrawal pipe 24. It is also feasible to have a gas withdrawal pipe which projects through the roof or lid of the cover.

In FIG. 1, the cover is illustrated in a raised position on the right-hand side of the drawing while on the left-hand side of the drawing, the cover is shown in a low or rest position.

Figure 2:
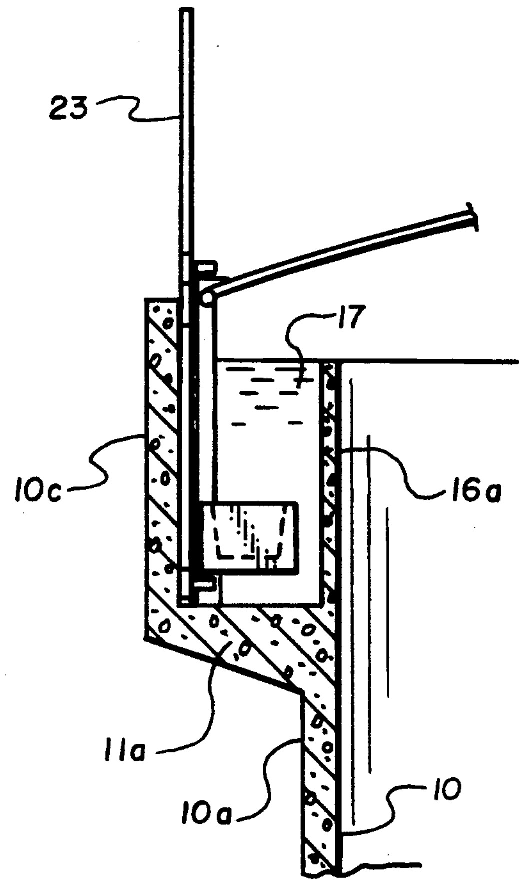
FIG. 2 is a partial, sectional, elevational view of a digester cover and tank of the instant invention with a separate buoyant chamber cantilevered outboard of the main tank wall.

In FIG. 2, which is a partial sectional elevational view of a digester cover and tank of the instant invention, a slightly different arrangement of the tank sidewall is illustrated. In FIG. 2, the main tank wall 10 is illustrated with the lower portion 10*a* below the corbel wherein the corbel 11*a* extends outboard of the main tank rather than inboard as illustrated in FIG. 1. Also in FIG. 2, the inner wall of the ballast bath 16*a* is constructed of concrete rather than a steel sidewall as illustrated in FIG. 1 and illustrated in FIG. 3. The upper wall 10*c* of the main tank is offset from the lower portion 10*a* by the width of the corbel. In the instant invention, the concrete extension member 11*a* which forms the base of the ballast bath 17 is referred to as a corbel even though it is a continuous member extending around the inside of the tank rather than being a number of discrete, separate members as has been traditional in the industry.

Figure 3:
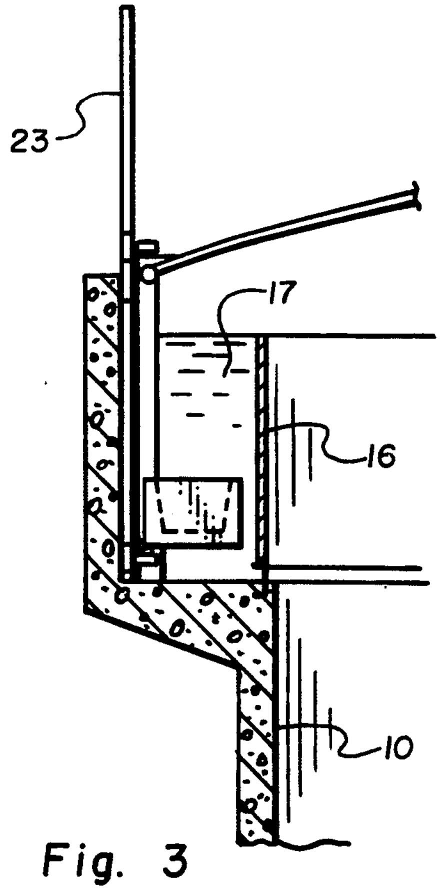
FIG. 3 is a partial, sectional, elevational view of a digester cover and tank having a slight variation in the buoyant chamber wall construction.

The elevational, sectional view illustrated in FIG. 3 is similar to that of FIG. 2 except that the interior wall is a steel wall as illustrated in FIG. 1. The construction of the main tank wall in FIG. 3 is the same as that in FIG. 2, and the advantages of such structure are several:

1. The corbel member may be supported by earth on the exterior of the tank and have the earth serve as a bearing load surface for the corbel member.
2. The ballast bath 17 is outboard of the main tank member 10 such that the gas-holding portion of the tank is expanded. Further discussion of this will occur in reference to later identified figures.

Figure 4:
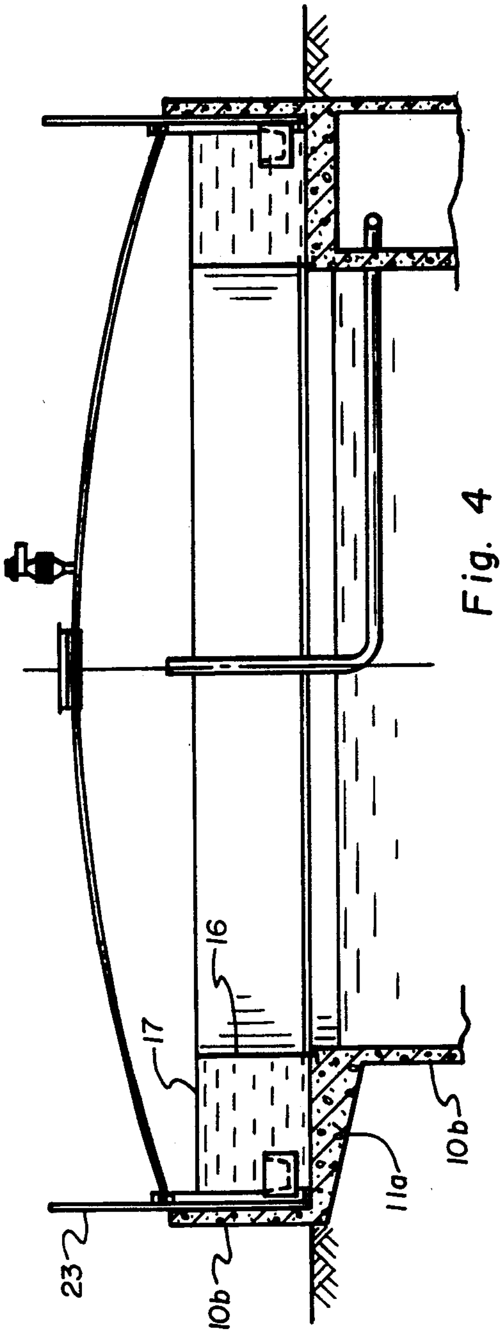
FIG. 4 is a partial, sectional, elevational view of a digester of the instant invention with a very large buoyant chamber and a large cover to provide large gas-holding capacity.

FIG. 4 illustrates a corbel member 11*a* which is similar to the corbel in FIG. 2 except that it is more horizontally extended, i.e., forms a wide base in the ballast bath. In the digester illustrated in FIG. 4, the main tank may be of a smaller diameter and hold less sludge in comparison to the amount of gas storage capacity. In certain digesters, the quantity of gas storage may be a primary consideration. Digester tanks such as that illustrated in FIG. 4 accommodate a large quantity of gas storage for a minimum sludge volume. In the digester of FIG. 4, the interior wall 16 forms one wall of ballast bath 17 wherein wall 16 is placed a considerable distance from wall 10*b* to allow extra working space between the ballast and wall member 16.

The digester of FIG. 4 has a buoyancy chamber (ballast bath) which has a large volume in comparison to the ballast volume. This has certain advantages and disadvantages, some of which are discussed hereinafter with reference to other features of the invention. A ballast bath with a large volume such as that illustrated in FIG. 4 add considerable weight to the structure when the ballast bath is filled with water. As is apparent from other embodiments illustrated herein, a ballast bath having a minimal size in comparison to ballast volume may require an overflow/refill system to achieve maximum cover travel.

A ballast bath, such as that illustrated in FIG. 4 wherein the bath volume to ballast volume may be 10:1 or even greater, does not require ancillary systems in order to achieve full cover travel. For example, in a ballast bath having such a 10:1 ratio, the level of buoyancy liquid would drop only 10 percent of the height of that portion of the ballast block which is emerged. Thus, for a large ballast block having a four foot height, the liquid level drop would be less than four inches with the ballast fully emerged.

In FIG. 4, the volume of stored gas for the same diameter of cover could be increased by the volume of the ballast bath by placing the ballast bath externally to the tank wall and having the ballast members mounted on the exterior of the sideskirt. Such external buoyancy chambers have several advantages, as expressed elsewhere herein, including minimizing the area of buoyancy liquid exposed to the humid corrosive gases. A large liquid surface exposed to $SO_2$, $H_2S$ and other such gas will absorb such gases over a period of time. The buoyant liquid may be treated, however, to neutralize the effect of such absorbed gases. Monitoring and treatment of buoyant liquids are easier with ballast baths which are external to the main tank.

Figure 5:
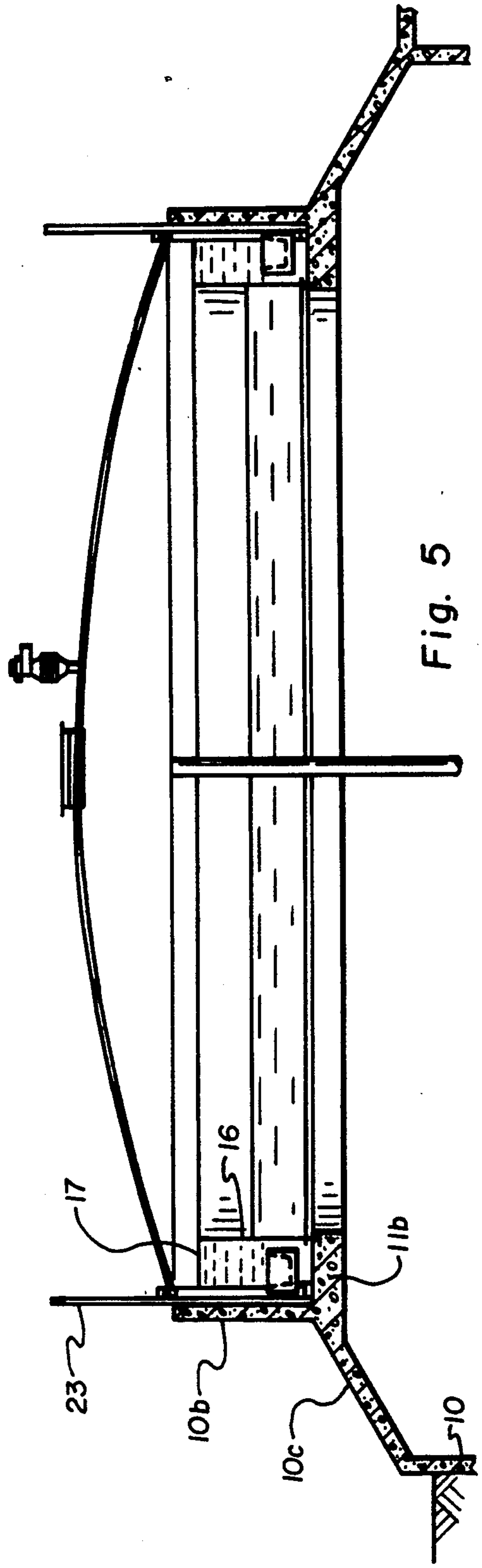
FIG. 5 is a partial, sectional, elevational view of a digester of the instant invention having a small cover in comparison to a large tank to provide large sludge-holding capacity.

Another digester tank is illustrated in FIG. 5 wherein the tank wall 10*a* has a much greater diameter than the upper tank wall 10*b*. Tank walls 10*a* and 10*b* are joined by sloping tank wall 10*c*. Corbel member 11*b* which is a continuous ring around the interior of the tank is positioned at the juncture of the upper tank wall 10*b* and sloped into tank wall 10*c*. Inner wall 16 is attached to corbel member 11*b* and along with tank wall 10*b* and corbel member 11*b* form the ballast bath 17. The structure of the digester tank in FIG. 5 is one in which the sludge volume is designed to be maximized with reference to the gas storage volume.

Figure 6:
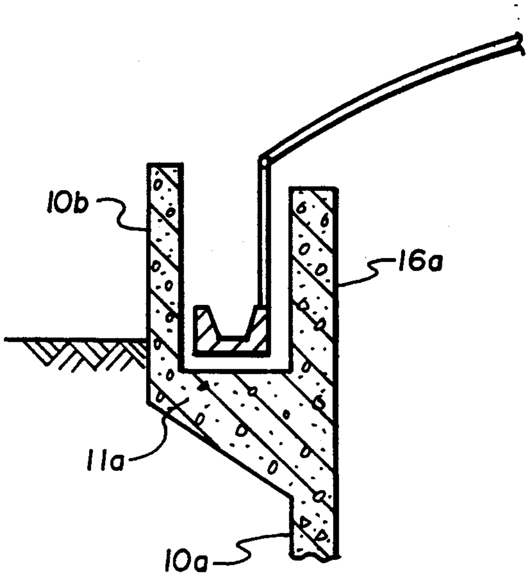
FIGS. 6 and 7 are partial, elevational, sectional views of digesters of the instant invention with buoyant chambers external to the inner tank wall with sideskirts adapted to hold ballast members on the exterior of the sideskirt.
Figure 7:
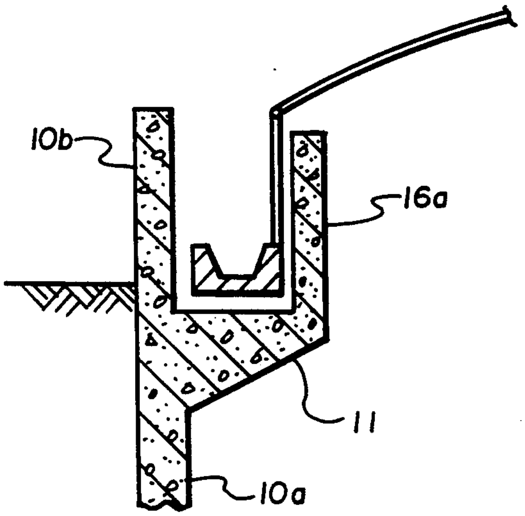

FIGS. 6 and 7 are elevation, sectional views of another embodiment of the instant invention wherein the buoyant liquid chamber is external to the main tank and structured in a manner that the ballasts can be attached to the outboard surface of the sideskirt. FIG. 6 illustrates an embodiment wherein the corbel member is directed outboard of the main tank wall 10*a* and has the advantage of being partially supportable by earth fill. In the embodiment of FIG. 6, the upper tank wall 10*b* and inner wall 16*a* are both formed with concrete, and the structure is an integral concrete structure of the upper wall 10*b*, the interior wall 16*a*, the corbel member 11*a*, and the main tank wall 10*a*. The structure illustrated in FIG. 7 is similar except that the corbel member is directed to the interior of the tank and is supported only by tank wall 10*a*.

Numerous advantages exist for having the ballast bath external to the main tank, that is with the ballast members on the outside of the sideskirt. For example, the density in the external liquid ballast bath 17*a* may be changed by adding heavy, soluble inorganic salts which will change the buoyancy of the liquid with reference to the concrete and will change the weight of the liquid in the ballast cavity. Different operating pressures for the gas-holder cover may be obtained by changing the buoyant liquid density. Also, the construction of the tank may be facilitated by an external chamber inasmuch as the cover may be completely constructed in place before the ballast members are attached. Also, it is easier to attach the ballast members inasmuch as they are positioned externally of the main cover. Monitoring of the buoyant liquid level, adding liquid, producing a liquid overflow, treating the liquid and like procedures are facilitated by an external buoyant chamber.

In construction of a cover such as that illustrated in FIG. 1, the metal plates which form the top cover 20 of the gas-holding cover cannot be all in place before the ballast members are lifted into place by a crane. However, in a structure such as that illustrated in FIG. 6, the cover roof may be completely made, welded to the sideskirt, and in fact, the liquid ballast bath or well may be filled with water and the cover pressure tested before the ballast members are added. Also, the use of the external well permits visual inspection of the water level in the well and even permits easier visual inspection of the ballast so that it would be known whether any ballast which have cavities have developed cracks and are perhaps not maintaining watertight integrity. Furthermore, ballasts may be easily removed and weight adjusted, e.g., smaller or larger ballasts can be readily substituted without taking digesters out of operation.

Figure 8:
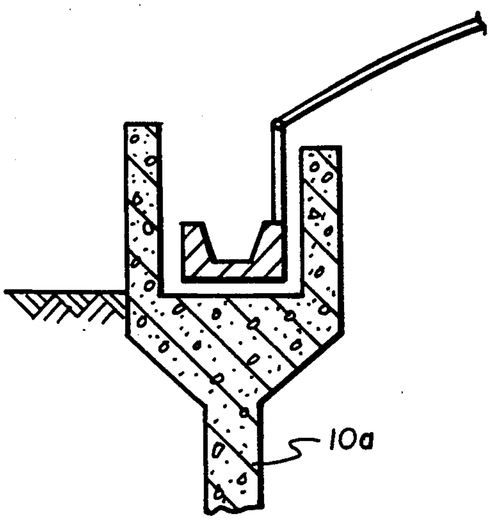
FIGS. 8 and 9 are partial, elevational, sectional views of digesters of the instant invention wherein the buoyant chamber is centered with respect to the lower portion of the main tank wall.
Figure 9:
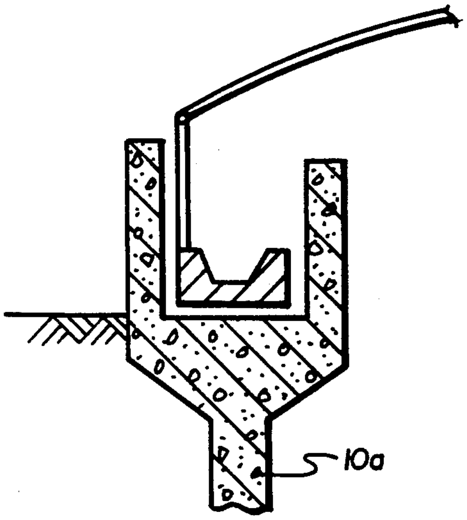

The digester tank designs of FIG. 8 and 9 are ones in which the buoyant liquid chamber, whether structured as an inner ballast bath or as an outer ballast bath, is positioned substantially directly over the main lower tank wall 10*a*. The addition of a buoyant liquid chamber sized to accommodate large ballast members adds considerable additional weight which the lower tank wall 10*a* must support. In a structure such as that illustrated in FIG. 17, the tank wall must support the weight of the roof including the ballast as well as the weight of the buoyant liquid chamber on the corbel member 11 which is cantilevered to the tank wall 10. In the older designs wherein the ballast members were immersed in the sludge, there was no buoyant liquid chamber, and the corbel members and tank wall had to support only the weight of the ballast and digester cover. For large tanks, the weight of the cover including ballast may be as much as 500,000 pounds or more. The weight of the water in a buoyant liquid chamber for a digester tank having a 100 foot diameter and five foot wide liquid chamber and having a height of ten feet defines a buoyant liquid volume of about fifteen thousand cubic feet which equates to nearly 1 million pounds of water. Thus, cantilevering that weight plus the weight of the cover including ballast as shown in structures illustrated in FIG. 7 may require a very thick concrete tank wall 10, especially at the lower portion and a very thick and strong corbel member 11. The structure illustrated in FIG. 6 may have advantages from a structural standpoint inasmuch as the corbel member 11*a* extends outboard of the main tank lower portion 10*a* and may be partially supported with earth fill since these tanks are frequently at least partially buried in the earth.

In instances where the tank may not be readily buried or the earth fill does not provide significant support, a tank structure such as that illustrated in FIGS. 8 and 9 may be advantageous wherein the buoyant liquid chamber is positioned with its geometric center substantially directly over the lower tank wall 10*a*. FIG. 8 illustrates a digester tank with an outer well while FIG. 9 illustrates a tank with an inner well. The tank wall structure, however, illustrated in FIGS. 8 and 9, is designed to optimize the strength of the structure rather than to affect the operating characteristics of a digester.

Figure 10:
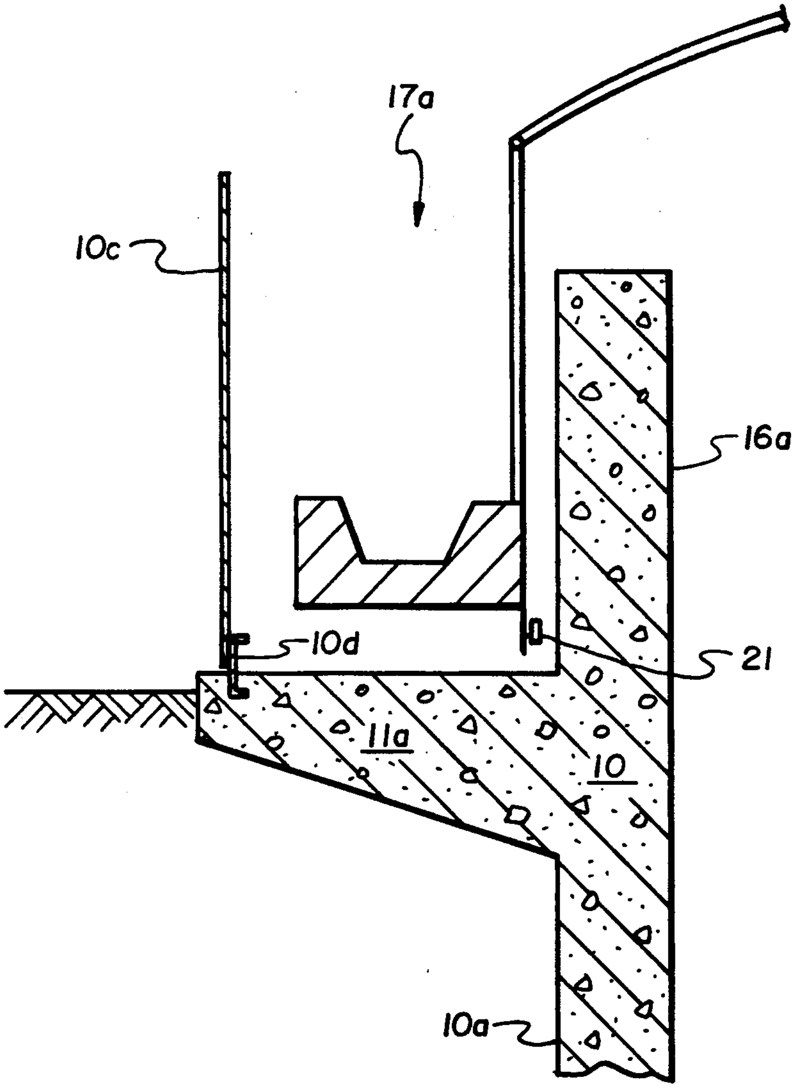
FIG. 10 is a partial, elevational, sectional view of a digester with an external buoyant chamber having an exterior, removable shell wall.

The tank wall structure illustrated in FIG. 10 provides a digester with certain advantages both in terms of construction, operation, and maintenance. Corbel member 11*a*, which is a continuous member circumscribing the exterior surface of the main tank wall 10, is integrally formed with the concrete inner wall 16*a* and the lower portion of the main tank wall 10*a*. A steel external wall 10*c* is attached to a flange member 10*d* which is embedded in the corbel member 11*a* near the free end or unsupported end of the corbel member. The structure illustrated in FIG. 10 is shown with the corbel member having earthen fill support to help support the load on the corbel.

A number of advantages accrue from the structure illustrated in FIG. 10. The digester tank wall 10 of concrete is usually formed first in the field then the cover is assembled and welded in place. In traditional digester tanks where ballast members go on the inside of the tank, the top of the cover must be left partially open so that the digester blocks may be lifted by a crane down onto the support members or, if the ballast is to be poured in place, then concrete must be pumped over the wall of the tank into a circular, annual form at the lower end of the interior of the sideskirt. However, with a structure such as that illustrated in FIG. 10, the cover may be completely assembled, including the sidewall, welded together and completely fabricated. The exterior wall 10*c* can be constructed later so that workmen have ready access to the external surface of the sideskirt without having to climb up over the external wall 10*c* and down into the ballast bath 17*a*. Thus, constructing exterior wall 10*c* as a last step has numerous construction advantages. The positioning of the ballast blocks may be done before wall 10*c* is in place so that these could be positioned by forklifts rather than through the use of cranes. Also, the individual ballast members could be readily cast in place either in a circular, continuous trough to form a solid ring of concrete or in separate ballast block forms.

The buoyant liquid chambers or ballast baths of the instant invention are large having a width of at least about three to five or more feet, a height of from about 8 to 15 feet and a circumference of about 150 to 450 feet. The walls of such chambers are predominately of concrete. A concrete wall of four inches to six inches in thickness for various sizes of digesters may weigh from about 200,000 pounds to about 1,000,000 pounds.

The buoyant liquid chambers or of the invention are large with respect to the tank. A launder trough or a seal trough merely for sealing purposes may be quite small in comparison. A launder trough is neither very deep nor very wide while a sealing trough may be relative deep for a telescoping gas-holding cover but is generally quite narrow.

The utilization of a buoyant liquid chamber separate from the sludge-holding portion of the tank provides numerous advantages. A particular advantage is that the sideskirt may be shorter since the rising and falling of the sludge level which required a deep skirt when the lower edge of the skirt is immersed in the sludge, is no longer a factor in sideskirt design. Shorter sideskirts save steel, which is desirable. Reducing the amount of steel in the sideskirt reduces the unballasted weight of the cover, thus necessitating more concrete ballast to achieve the higher operating gas pressures required in modern sludge digesters. Additional concrete ballast will generally result in ballast members which are wider thereby necessitating very wide buoyant liquid chambers.

A further advantage of the separate buoyant liquid chambers is the non-corrosive nature of the liquid, typically water, used in such chambers. The problems of corrosion and erosion caused by immersion in sludge are avoided. Also, no sludge is exposed to the atmosphere, and when the sideskirt is in an elevated position, an unsightly sludge-stained external surface is not exposed. The chamber also acts as a seal against escape of gas. While a very narrow chamber could accomplish that purpose, a wide chamber is required in the instant invention to accommodate the large ballast members used in modern gas-holding sludge digesters.

Another advantage of a separate buoyant liquid chamber is that the density (specific gravity) of the liquid may be modified. For example, a liquid other than water could be used. Also, the specific gravity of water may be increased by adding of soluble salts. Such salts as barium chloride may be used to increase the specific gravity as high as 1.3.

In the event adding of salts creates a concern over corrosion, cathodic protection may be readily employed to protect metal parts immersed in the buoyant liquid. Such protection could not be as readily used to protect metal parts immersed in sludge.

The ballast bath digesters of the instant invention readily facilitate use of ballast members of the type disclosed in Cook, et al., U.S. Pat. No. 4,391,705. However, conventional solid, concrete block ballasts may be employed as well as lightweight concrete ballast blocks. Also, continuous ballast rings formed from concrete may also be utilized. Also, use may be made of various composite ballasts such as a concrete block combined with an air chamber.

The walls of the main digester tank as well as the ballast bath may be made of concrete or steel or some combination of the two or of fiberglass reinforced plastic.

The utilization of a separate buoyant chamber, generally denominated herein as a "ballast bath," to provide a buoyant liquid separate from the sludge liquid to interact with the cover ballasts, enables a sludge digester to be operated in a more flexible, less polluting manner. The arrangement also makes certain monitoring and maintenance procedures easier and more effective.

As illustrated in the attached figures, the sideskirt depending from the roof of the cover rides very close to one wall of the buoyant liquid chamber. In FIG. 1, the sideskirt, similar to the sideskirt in Cook, et al., is proximate to the inside surface of the exterior wall of the tank. This facilitates interaction of the cover via rollers 21 and 22 with guide post 23.

In FIGS. 2 and 3, the sideskirt is proximate the inside surface of the external wall of the buoyant chamber. A guide system similar to that illustrated in FIG. 1 is used in the device of FIGS. 2 and 3. In contrast, the sideskirt of the device of FIG. 10 is proximate to the outside surface of the main tank wall. A roller 21 uses the outside surface of the main tank wall as a guide. The ballast member 12 of FIG. 1 and the ballast members of the other figures is cantilevered from the sideskirt and occupies most of the width of the buoyant liquid chamber. Such an arrangement, however, may require another guide system to interact with an upper roller guide.

The close proximity of the sideskirt to one wall of the buoyant liquid chamber and its remote spacing from the other wall of the buoyancy chamber is in contrast to previous structures wherein a circumscribing well was used for sealing purposes with a fixed or telescoping cover, such as that disclosed in Bohnhardt, et al. or Anderson, supra. Also, in structures such as that described and disclosed in Bohnhardt, et al. and Anderson, the cover roof generally rested upon the upper edge of the tank wall. In contrast, the buoyant liquid chamber illustrated herein has a floor which serves as a corbel providing a support for the ballast and cover. The lower edge of the sideskirt or a structural extension thereof rests on the corbel (chamber floor) and supports the cover.

The telescoping cover of the instant invention preferably interacts with guides which are external to the digester. In Bohnhardt, et al. and Anderson, internal guide posts and complementary tubes (pipes) were used which, if structured of steel, could result in sparks if the steel post and steel tube were caused to rub against one another, e.g., when under a wind load while the cover was traveling up or down. In a volatile hydrocarbon vapor atmosphere, sparks can be especially hazardous.

Internal guides are generally undesirable as being inaccessible for repair and the possibility of creating a hazardous condition. Typical guide means include rollers interacting with a vertical support. Rollers may be broken or wear out, especially when exposed to the toxic, corrosive atmosphere contained within a digester. Replacement of worn or broken rollers, if such are internal to the digester, requires that the digester be shut down, a time-consuming and expensive procedure.

The instant invention, unlike prior uses of sealing wells, uses a deep, wide liquid chamber as a buoyancy chamber for large ballast members supported at the lower edge of a digester cover sideskirt utilizing external guide means.

The instant invention is particularly well-suited to the use of external guide means which are remote from the corrosive and erosive environment found inside a sludge digester. The instant invention, when an internal ballast is used, i.e., a ballast located internally on the inside wall of the sideskirt, can be fitted with guide rollers which attach to the outside surface of the sideskirt, usually at the top and bottom edges, to interact with a guide post such as that illustrated in FIG. 1. The height of the guide post can be predetermined to provide a guide track for the entire vertical rise of the cover.

Although this guide system is similar to that used on a Cook, et al. digester, the rollers are remote from any sludge or corrosive environment. The lower guide roller of Cook, et al. is always immersed in the sludge liquid. To repair or replace a lower roller in the Cook, et al. digester, it is necessary to shut down the digester, vent all gas, and lift the cover to a level above the main tank wall so that the lower rollers can be accessed.

The digesters of the instant invention employing a buoyancy chamber separate from the main tank chamber provides many advantages as well as devices and adaptations not found in digesters where the ballast submerges and emerges from the sludge in the main tank.

The volume of sludge in a tank is very large in comparison to the volume of even very large concrete ballast blocks frequently used in typical high-pressure gas sludge digesters. Thus, the emergence of ballast from the sludge causes only an imperceptible change in the level of the sludge.

The sludge volume, because of differences in sludge inflow and discharge, does not remain constant, and the sludge level rises and falls which results in the cover rising and falling even during conditions of constant gas volume at a constant pressure. The instant invention provides an advantage inasmuch the rising or falling of the sludge level does not necessarily affect ballast position and, consequently, cover position. The rising of the sludge level during conditions of maximum gas storage at an elevated pressure may result in such a pressure increase that gas will be released, i.e. lost, through the relief valve.

In contrast, the volume of liquid, usually water, in the separate buoyancy chamber is relatively small in comparison to ballast block volume. Thus, as the ballast emerges, the level of the buoyancy liquid drops significantly unless liquid, preferably water, is added at a rate equivalent to rate of ballast volume emergence. If liquid is not added, then a contradictory condition occurs. Emergence of the ballast is caused by increasing gas pressure under the cover. If the liquid in the buoyancy chamber is allowed to drop, then the total volume of gas which can be stored for a given emerged ballast condition is significantly less than if the buoyant liquid level were to be maintained at the same level as when the ballast is submerged (see FIGS. 11 and 12).

Maintaining a constant buoyancy liquid level during ballast emergence requires drain means to prevent an overflow condition when the ballast resubmerges.

Thus, the buoyancy chamber is preferably equipped with liquid level detection means which detects a dropping of the liquid level during ballast emergence and activates filling means. As the ballast resubmerges, drain means is provided to maintain a constant, predetermined liquid level in the buoyancy chamber.

The instant invention involves a number of embodiments. The ballast baths represented in FIGS. 11(*a*) and 11(*b*) illustrate two digesters wherein operating pressure is achieved, e.g., twelve inches water column, but with the cover resting on the corbels which is considered a no-gas-storage condition.

Figure 11A:
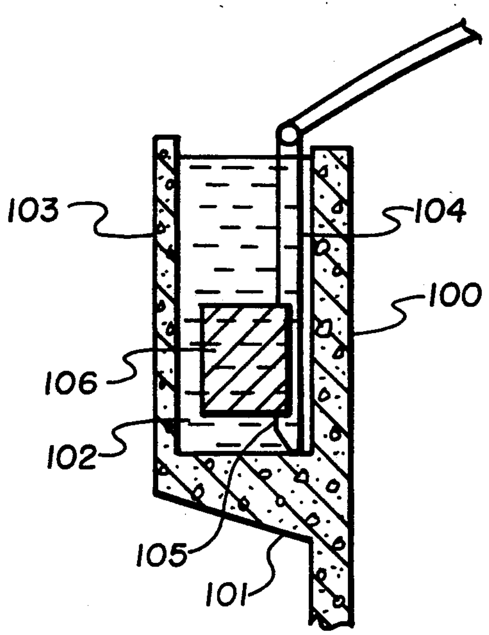
FIGS. 11(*a*) and 11(*b*), respectively, illustrate partial, elevational, sectional views of digesters with ballast members submerged in buoyant chambers without and with overflow means and liquid addition means.
Figure 11B:
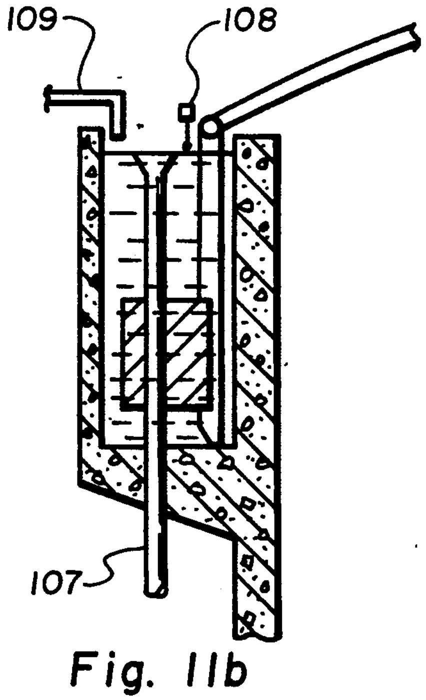

The digester of FIG. 11(*a*) has a main tank wall 100 to which a cantilevered, external corbel 101 forms the base of a ballast bath 102 in conjunction with bath wall 103. The cover sideskirt 104 at its lowest edge is resting on the corbel 101 and is supporting a ballast support member 105. As gas evolves under the cover, gas storage occurs, and ballast block 106 rises in the ballast bath. No change in operating pressure occurs until the ballast member begins to emerge from the ballast bath liquid. Thus, in FIG. 11(*a*), the operating pressure remains constant from the ballast position shown in FIG. 11(*a*) until the top of the ballast block reaches the predetermined level of liquid in the ballast bath. If the height of the ballast bath liquid is, for example, twelve feet and the height of the block from the corbel is four feet, then the sideskirt can travel a distance upwardly a distance of about eight feet to increase many fold the volume of gas stored under the cover while maintaining a substantially constant operating pressure.

The ballasted digester in FIG. 11(*b*) is substantially identical to the device shown in FIG. 11(*a*) except that the ballast bath has been equipped with an overflow drain 107, a liquid level sensor 108, and a liquid refill device 109 which is operatively connected to the liquid level sensor 108. A float ball valve similar to that used in toilet tanks may be employed as a sensor and refill whereby the float drops to open a valve (not shown) to direct liquid from a main liquid supply line to the interior of the ballast bath.

Although the device of FIG. 11(*b*) has refill means and an overflow, its operation in the condition shown in FIG. 11(*b*) is the same as that in FIG. 11(*a*) until the gas storage volume increases to the point that the top of the ballast block begins to emerge from the predetermined liquid level of the ballast bath.

Emergence of the ballast from the liquid in the ballast bath causes differences to occur in operating pressure and gas storage with the systems involved in FIGS. 11(*a*) and 11(*b*) operating differently, especially at the extreme condition wherein the ballast block is fully emerged from the liquid in the ballast bath.

Figure 12A:
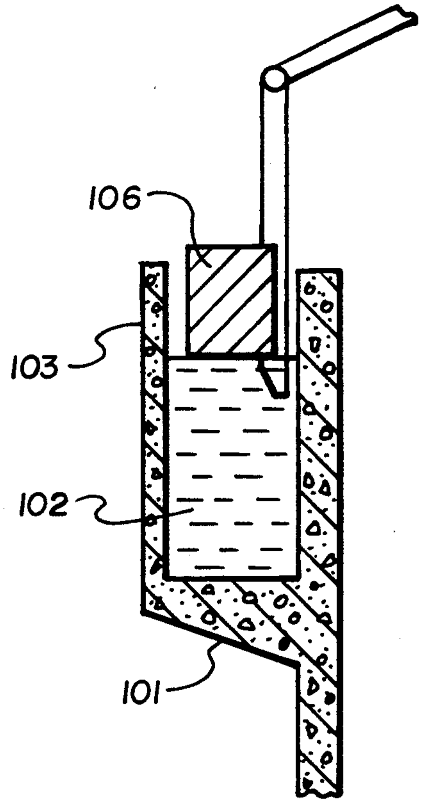
FIGS. 12(*a*) and 12(*b*) illustrate the digester buoyant chambers, respectively, of FIGS. 11(*a*) and 11(*b*) with the ballast members in an unsubmerged condition.
Figure 12B:
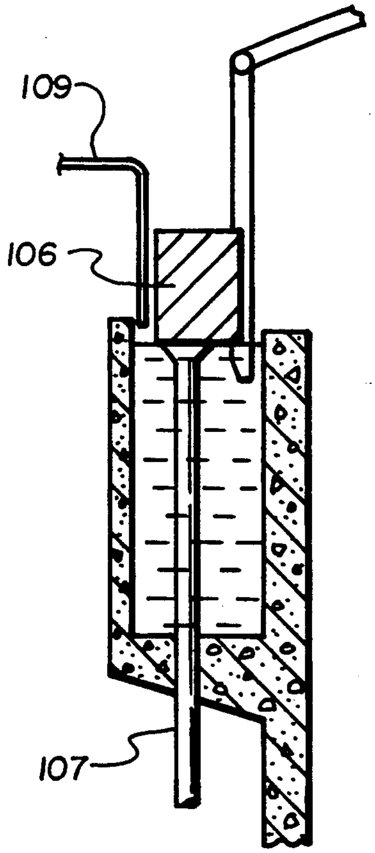

FIGS. 12(*a*) and 12(*b*) represent the digesters of FIGS. 11(*a*) and 11(*b*), respectively, with the ballast members fully emerged. In FIG. 12(*a*), the liquid level in the ballast bath has dropped considerably below the level shown in FIG. 11(*a*). Because of the high pressures, e.g. 12 inches or more, developed in modern gas digesters coupled with the modern lightweight steel roofs, considerable concrete ballast is used to provide the total weight needed to achieve the required gas pressures. Thus, the volume of concrete ballast oftentimes is 10 percent to 30 percent or more of the volume of the liquid in the ballast bath.

In FIG. 12(*a*), the drop of liquid level may, for example, be from 10 percent to 30 percent or more, lower than the level in FIG. 11(*a*) which means that the sideskirt upward travel is restricted by the drop in liquid level because further upward travel permits the release of gas under the lower edge of the sideskirt. For example, a ballast bath having an original twelve foot liquid level depth in FIG. 11(*a*) may experience a three foot drop in the liquid level as shown in FIG. 12(*a*).

The advantage of sensing the ballast bath liquid level and adding refill water to maintain a predetermined level is illustrated in FIG. 12(*b*). Since the water level remains the same, as illustrated in FIGS. 11(*b*) and 12(*b*), at its highest level at any stage of ballast submergence or emergence, the liquid level sensor 108 would immediately sense any dropping of the liquid level in the ballast bath thereby initiating the refill mechanism 109 to maintain the predetermined (maximum) liquid level. When the ballast is fully emerged, which is not a usual operating condition, the total volume of liquid added to the ballast bath is equal to the volume of the ballast, ballast supports, etc.

The quantity of ballast, typically as concrete ballasts, may vary widely depending upon the size of the digester and the specified operating pressures. For small digesters, i.e., those from 40 to 80 feet in diameter, the ballast weight may be under 150,000 pounds which equates to about 1,000 cubic feet of ballast. For larger digesters, e.g., digesters greater than 80 feet in diameter and especially for digesters over 100 feet in diameter which tend to be typical in the industry, the volume of ballast will often exceed 5,000 cubic feet and a weight of concrete of over 750,000 pounds. Thus, in a large digester as much as 5,000 cubic feet (approximately 40,000 gallons) of water would be required to be added to the ballast bath when the ballast is fully emerged in order to maintain the predetermined (maximum) liquid level and achieve the maximum amount of gas storage.

The addition of water or other selected buoyant liquid to the ballast bath during ballast emergence increases the volume of gas stored for a given size of digester. This can be seen in FIGS. 12(*a*) and 12(*b*) inasmuch as the cover in FIG. 12(*a*) cannot elevate as high at the point of full emergence as the cover is FIG. 12(*b*).

Figure 13A:
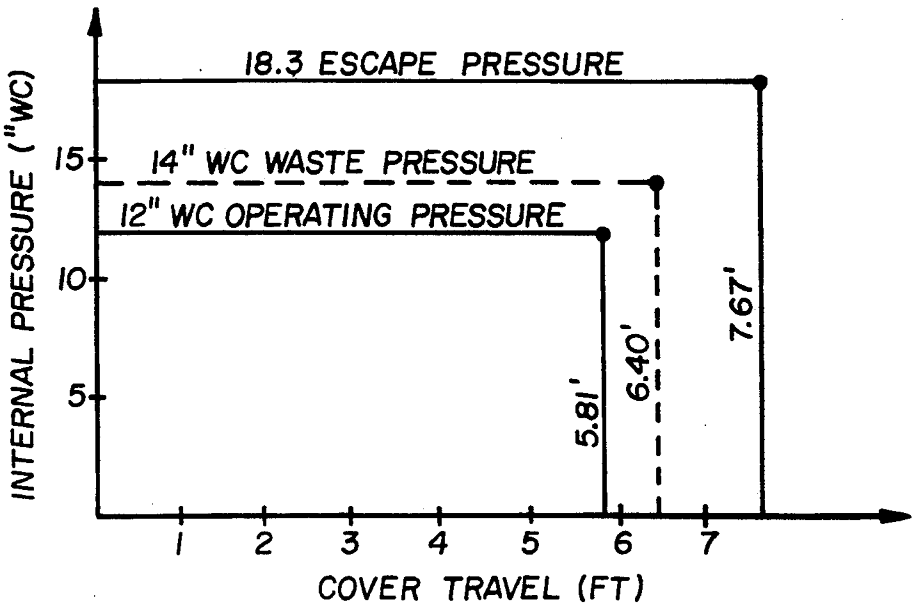
FIGS. 13(*a*) and 13(*b*) are charts illustrating, respectively, the comparative travel of the digester covers for the digesters illustrated in FIGS. 11(*a*) and 12(*a*) compared with that of FIGS. 11(*b*) and 12(*b*)
Figure 13B:
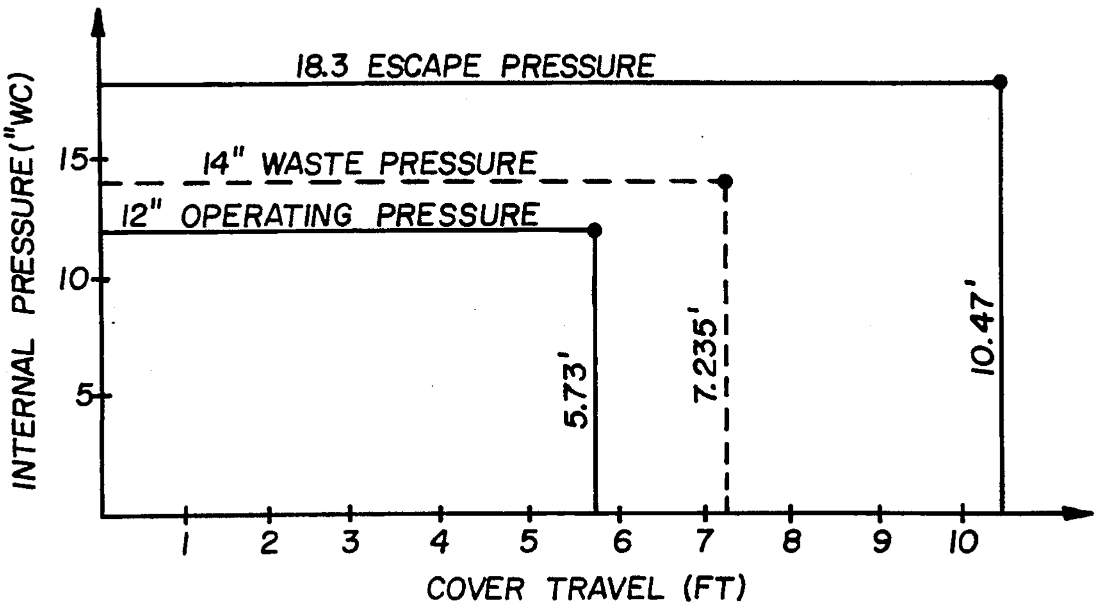

The difference in storage capacity of a given digester is illustrated in FIGS. 13(*a*) and 13(*b*).

FIG. 13(*a*) illustrates the actual cover travel in feet for a digester having a sideskirt maximum travel capability of about twelve feet with a sideskirt length of about thirteen feet and a ballast bath without any refill mechanism.

In FIG. 13(*a*), the cover can travel upward about 5.8 feet before the ballast block begins to emerge. Thereafter, as the ballast emerges and the liquid level in the ballast bath simultaneously drops. The cover travels only to a maximum distance of about 7.7 feet before gas begins to escape under the cover.

Although a digester having ballast bath refill means experiences the same cover will travel about the same distance as a cover of FIG. 11(*a*) configuration during the normal operating pressure, i.e., wherein the ballast travels from the bottom of the ballast bath to incipient emergence, it travels a much greater distance during emergence of the ballast. As readily noted, the pressure increase for a digester of FIG. 12(*b*) configuration follows a more shallow linear slope in FIG. 13(*b*) than in FIG. 13(*a*). Thus, for a digester of FIG. 12(*b*) configuration at full emergence, the cover travel is about 10.5 feet which is the full height of cover travel (12 feet) less the 18 inch water column.

Frequently, digesters are operated at an "overpressure" which is a pressure generated with the ballast partially emerged. In the graphs of FIGS. 13(*a*) and 13(*b*), a nominal operational overpressure of 14 inches water column is selected. At such pressure, gas from the digester may be diverted to a waste boiler or for other uses. In FIG. 12(*a*), the digester without refill reaches 14 inches of pressure at a sideskirt travel of about 6.4 feet (FIG. 13(*a*)), while with refill means (FIG. 12(*b*)), the sideskirt travels about 7.2 feet (FIG. 13(*b*)). Typically, covers are not operated at pressures above their preselected overpressure operation. Thus, for a given digester having a ballast bath of the instant invention, the difference in gas storage volume is about 15 percent greater for a cover with a refill system than one without. For large covers, this can amount to a very large volume differences. For example, for a cover with a nominal diameter of about 120 feet, the difference may be as great as about 10,000 cubic feet.

Typically, the safety release valve will be set below the pressure at which gas escapes under the sideskirt. For example, for a cover having an escape pressure of eighteen inches, the safety relief valve may be set at about sixteen inches. A further advantage of the cover illustrated in FIGS. 11(*b*), 12(*b*), and 13(*b*) is that a much larger volume of gas is held at the relief pressure. For example, a cover having a nominal diameter of 115 feet stores about 108,000 cubic feet at an escape pressure of eighteen inches in comparison to storage of less than 80,000 cubic feet for the same cover but in a configuration shown in FIGS. 11(*a*), 12(*a*), and 13(*a*) at the same escape gas pressure. Thus, in the event of relief valve failure, a greater amount of time is permitted, assuming the same rate of gas generation for the digesters, to make some manual correction to relieve the gas pressure. (Permitting gas, which is explosive and toxic, to escape under the edge of the sideskirt is generally a hazardous condition and avoided through proper operating procedures.)

Gas-holding digesters of a conventional type have a telescoping cover which fits closely within the main tank. High-pressure gas holders of this general type are illustrated and described in Cook, et al. Telescoping digester covers require guide means to guide the cover to maintain alignment during its vertical travel.

The digesters of the instant invention also require guide means, however, the innovative features of the instant invention are generally not adaptable to conventional guide systems. For example, in the Cook, et al. digester, the inner sidewall of the main tank acted as a guide surface for the lower guide roller which is always immersed in sludge.

Figure 14:
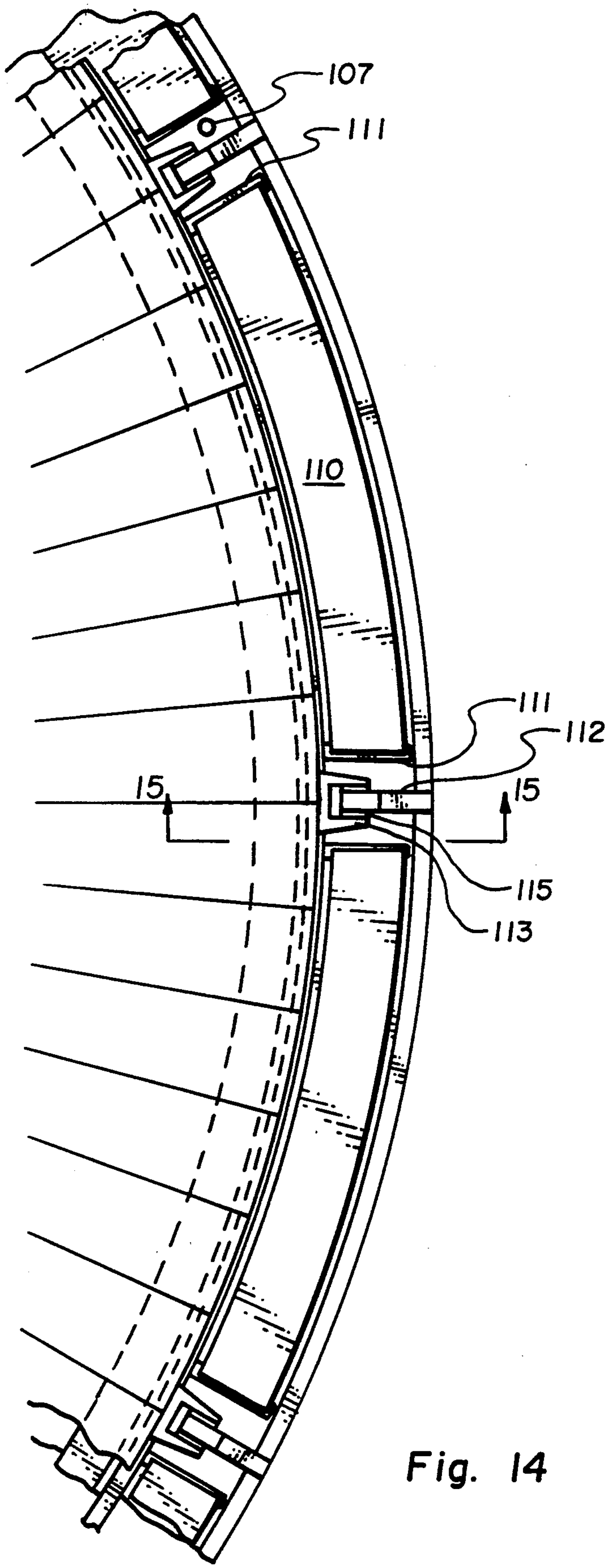
FIG. 14 is a partial plan view illustrating a digester of the instant invention with unique guide means.
Figure 15:
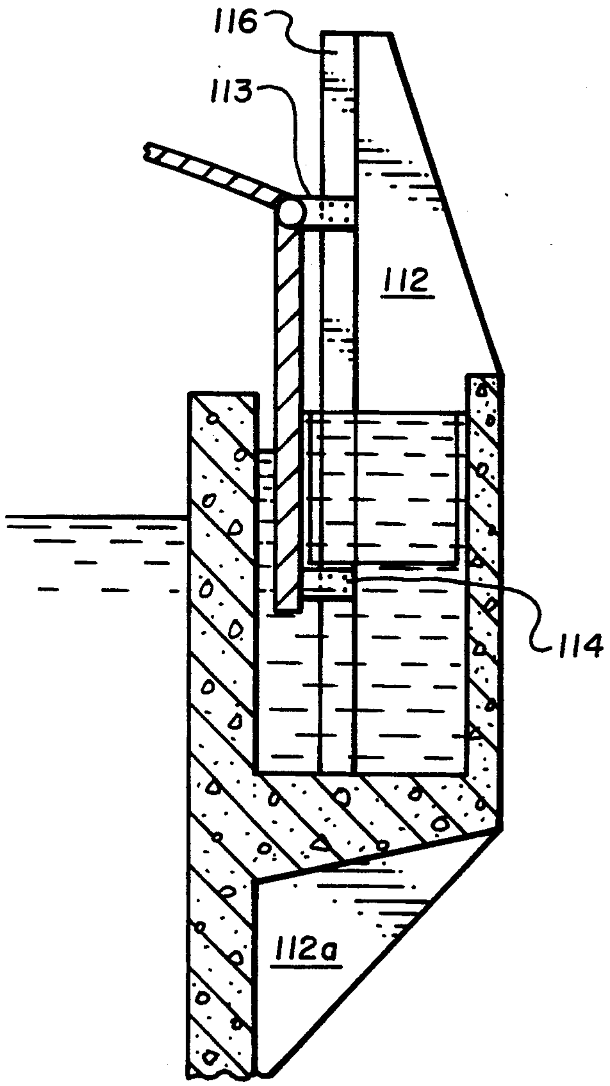
FIG. 15 is a partial, elevational, sectional view of the guide means of FIG. 14 along section lines A—A of FIG. 14.

A unique guide system for guiding the innovative covers of this invention is illustrated in FIGS. 14 and 15. FIG. 14 is a partial plan view illustrating a gas-holder cover 20 to which large curved ballast blocks 110, preferably of concrete, are attached. The ballast blocks in this embodiment are curved to conform to the shape of the ballast bath 102. Preferably, the ballast bath is as narrow as possible so that a minimum of water and concrete structure are used in the ballast bath in order to minimize weight and extra structure. Curved ballast blocks accomplish this purpose. Also, a large number of short (stubby) blocks accomplish that purpose although requiring a large number of ballast supports.

The curved ballast blocks illustrated in FIG. 14 are large, occupying approximately 30° of the cover circumference. These blocks may be cast in place into a curved trough (not shown) or precast and positioned on ballast supports 111. Between each pair of ballast members is a guide column 112.

The guide columns 112 are preferably made of concrete and are positioned at spaced locations around the circumference of the tank. The spacing is preferably uniform and is approximately 30° for the structure illustrated in FIG. 14. A guide column may be relatively thin, especially if it is reinforced, thicknesses from about three inches to about twelve inches, depending upon the number of guide columns used and the size of the cover, are usually adequate. Generally, at least four guide columns spaced 90° from one another are used, although preferably at least six columns equidistantly spaced from each other are utilized on large digesters.

The guide columns 112 are of a sufficient height to accommodate the uppermost travel of upper guide means 113. Thus, for a cover having a maximum upward travel of twelve feet, the guide column 112 will extend about 12 feet above the top of the main tank wall. The guide columns 112 of FIG. 15 extend below the ballast bath and are supported by a concrete web 112(*a*) which forms the base of the column. The column base 112(*a*) may also be structured to add support to the ballast bath.

The guide means 113 and 114 are "U"-shaped members attached at upper and lower positions on the cover sideskirt 19. Preferably, the guide means are spaced as far apart as possible to maximize the stability of the cover during its travel. The guide means 113 and 114 have wear pads or shoes 115 which contact a wear surface (plate) 116 on each side of the guide column. If the column is concrete, the wear surface 116 is preferably of steel or other suitable smooth metal, hard plastic or other strong, rigid material. The steel wear surfaces may be sufficiently thick so that they may be skimmed to provide true vertical surfaces. The wear shoes 115 are preferably replaceable.

Having an external guide column and external guide means is advantageous since the guides 113 and 114 are much more accessible than when an the internal guide is immersed in sludge. The external guide shoes 115 are preferably a long wearing, smooth plastic material such as teflon, polypropylene, nylon, and the like. Conventional roller guides can be utilized wherein the rollers are oriented to contact either the front surface of the guide column or with the side surfaces as illustrated in FIGS. 14 and 15. The "U"-shaped guides prevent the cover from rotating.

The spacing between adjacent ballast members in a structure such as that illustrated in FIG. 14 is preferably such that a repairman could easily repair or replace guides 113 or 114 or replace shoes 115 Or, if necessary, adjust wear surfaces (plates) 116. This ready access to the guides, especially the lower guide, is a great advantage over conventional digesters wherein the lower guide was located in the digester sludge. In such conventional digesters, replacement of a lower guide required that the digester be shut down, that its gas content purged with fresh air and its sludge level be lowered below the corbels. Even under the best of circumstances, changing a lower guide in a conventional digester is a dirty, time-consuming, inefficient operation.

Digesters of the instant invention having external guide systems are adaptable to changes of guides, wear surfaces, and the like without ceasing operation of the digester. The digester cover can be locked in place, continue to digest sludge, and to collect evolved gas and direct said gas to other equipment in the plant. The gas pressure could be monitored and withdrawn at a rate to maintain safe pressures well below the relief valve settings. Sufficient water would be retained in the ballast bath to maintain a liquid seal. It could be necessary, however, for a repairman to work on a guide submerged in six inches of water, which could readily be done.

It is preferred generally to have the guide column closely adjacent the sideskirt so that the guides 113 and 114 may be short in length. Alternatively, the guides could be elongated members adapted to cooperate with a guide column having its closest surfaces remote from the sideskirt, for example, where the guide column had its guide surface close to the outer wall of the ballast bath. Such extended guides would have to be structurally reinforced to handle the increased forces due to their extended moment arm.

Verticality of the guide column is very important. While wear surfaces can be thick plates which can be skimmed to accommodate irregularities in the column surface or slight departures from verticality, large departures from verticality are generally to be avoided. Thus, the guide columns are preferably substantially vertical, especially as to any surface which is a "guide" surface which could be the face or sides of the column.

In the embodiments illustrated and described herein, the ballast members are attached directly via support arms or the like to the sideskirt near its lower edge. Such a structure is preferred, however, the ballast could be attached to separate structures affixed to the roof members to support the ballasts in both submerged and emerged conditions with respect to the separate buoyancy chambers. For example, a cantilevered arm extending from the roof could be utilized to support the ballast members by means of a rigid dependency structure or by means of chains or cables. With such alternative ballast supports, the position of the ballast members would preferably be at or near the lower edge of the sideskirt.

The ballast members used in the instant invention may be of any convenient shape. Typically, solid concrete ballasts are used with a block shape with a length generally much greater than its width or height. Typically, the width of the ballast member is about the same as its height, i.e., a substantially square cross-section. Other shapes, of course, can be used wherein the ballast width is significantly greater than its height or vice versa. Also, of course, the ballast members may be equipped with cavities which contain liquid, such as those described in the Cook, et al. patent. Such ballasts may have open cavities or cavities which are sealed so that the liquid in the cavity is prevented from contacting the liquid in the buoyancy chamber.

Anaerobic sludge digesters digest organic waste by bacterial action. Generally, an operating temperature of 80° to 100° F. is required with optimum operating temperature rising about 95° F. The reaction (digestion) is generally exothermic, however, insulated tanks and heaters are often required for effective operation during the winter season in temperate climate regions. Thus, in northern climates, an internal buoyancy chamber, such as FIG. 1 or FIG. 4, may be preferred since the liquid in the chamber, typically water, would be maintained well above its freezing point. Such internal chambers may reduce the amount of gas storage capacity by displacing gas volume with liquid volume. Such concern did not exist with the digesters of the Cook, et al. type.

Digesters with buoyancy chambers in northern climates may require heaters in the buoyancy chambers or the addition of antifreeze chemicals such as ethylene glycol, salts, etc. The external chambers are preferably insulated when digesters are installed in northern climates so that heat from the digester assists in maintaining the buoyancy liquid above its freezing point. Also, a blanket of foamed styrene pellets or the like could be placed on the surface of the buoyancy liquid to further insulate the liquid from the cold environment.

Digesters are part of a sewage treatment plant and operate on a year-round schedule. Digestion temperatures must be maintained for efficient digestion whether it is winter or summer. Gas evolves from the digestion so that the gas-holding cover must function the same in winter as in summer whether the digester is located in Minneapolis or Miami. In contrast, gasoline or other petroleum products storage facilities do not have contents undergoing reaction, and the very low temperatures experienced in winter in northern climates would lower the vapor pressure of the petroleum products to such a low level that seals, such as those illustrated in Bohnhardt, et al., would not be required. Thus, the water in such seals could be drained during winter operation, or the seal water could be allowed to freeze if there was no concern about the resulting ice cracking the seal wall.

Various embodiments of the instant invention are described and illustrated herein, however, they are not intended to limit the invention which is defined within the scope of the appended claims.

We claim:

1. A ballasted, gas-holding, liquid sludge digester comprising:
 a main liquid sludge tank having a bottom wall and upwardly projecting sidewall;
 a cover having a top and depending sideskirt structure which telescopes with respect to the upwardly projecting sidewall of the main tank;
 ballast supported near the lower edge of said sideskirt;
 a ballast-engaging, liquid-containing well joined to said sidewall of said main tank such that said cover provides a gas-tight seal when said ballast interacts with liquid in said well so as to be partially emerged or fully submerged in the liquid;
 liquid fill means interacting with said well to maintain a predetermined liquid level in the well when said ballast is at least partially emerged from the liquid in said well; and
 overflow means interacting with said well to maintain a predetermined liquid level in the well when said ballast is submerged in the liquid in the well.

2. The digester of claim 1 wherein said well circumscribes said main liquid sludge tank.

3. The digester of claim 1 wherein said overflow means is in a fixed relationship to said well.

4. The digester of claim 1 wherein said liquid fill means has liquid level sensing means to determine the level of liquid in said well.

* * * * *

UNITED STATES PATENT AND TRADEMARK OFFICE

CERTIFICATE OF CORRECTION

PATENT NO. : 5,238,844

DATED : August 24, 1993

INVENTOR(S) : Wight, et al

It is certified that error appears in the above-indentified patent and that said Letters Patent is hereby corrected as shown below:

Column 5, line 65, change "FIG. i" to --FIG. 1--.

Column 16, line 53, after "115" change "Or" to --or--.

Signed and Sealed this

Twenty-first Day of February, 1995

Attest:

BRUCE LEHMAN

Attesting Officer

Commissioner of Patents and Trademarks